(12) United States Patent
Pacey

(10) Patent No.: US 10,940,282 B2
(45) Date of Patent: *Mar. 9, 2021

(54) SECRETION CLEARING PATIENT AIRWAY MANAGEMENT SYSTEM

(71) Applicant: Foster Pepper PLLC, Seattle, WA (US)

(72) Inventor: John Allen Pacey, Vancouver (CA)

( * ) Notice: Subject to any disclaimer, the term of this patent is extended or adjusted under 35 U.S.C. 154(b) by 448 days.

This patent is subject to a terminal disclaimer.

(21) Appl. No.: 15/807,148

(22) Filed: Nov. 8, 2017

(65) Prior Publication Data

US 2018/0318535 A1  Nov. 8, 2018

Related U.S. Application Data

(63) Continuation of application No. 14/165,317, filed on Jan. 27, 2014, now Pat. No. 9,839,755, which is a (Continued)

(51) Int. Cl.
*A61M 16/04* (2006.01)
*A61M 16/00* (2006.01)
(Continued)

(52) U.S. Cl.
CPC .... *A61M 16/0463* (2013.01); *A61M 16/0051* (2013.01); *A61M 16/0057* (2013.01);
(Continued)

(58) Field of Classification Search
CPC .......... A61M 16/0051; A61M 16/0057; A61M 16/04; A61M 16/0409; A61M 16/042;
(Continued)

(56) References Cited

U.S. PATENT DOCUMENTS 3,682,166 A    8/1972   Jacobs
3,815,606 A    6/1974   Mazal
(Continued)

OTHER PUBLICATIONS

Non-Final Office Action, U.S. Appl. No. 12/158,669, dated Mar. 16, 2012, pp. 16.
(Continued)

*Primary Examiner* — Kathryn E Ditmer
(74) *Attorney, Agent, or Firm* — Foster Garvey PC

(57) ABSTRACT

A pulmonary secretion clearing airway structure and related airway management system is disclosed that has a double lumen portion which each lumen of the double lumen portion operably secured to an airway management system so that inspiratory fluid (air/oxygen mixtures, with or without added water vapor) is delivered to the distal end of the ventilation catheter through one of the two lumens and expired inspiratory fluid, pulmonary secretions, and pulmonary fluids are removed from the patient through the other lumen. The expiratory fluid pathway preferably includes a secretion collection system for removing the pulmonary secretions and the like from the pathway, thereby improving operation and safety of the system. The airway structure can be a ventilation catheter or a supraglottic airway system such as laryngeal mask and the like.

10 Claims, 8 Drawing Sheets

Related U.S. Application Data continuation of application No. 12/158,669, filed as application No. PCT/IB2006/004079 on Dec. 21, 2006, now abandoned.

(60) Provisional application No. 60/752,108, filed on Dec. 21, 2005.

(51) Int. Cl.
*A61M 16/20* (2006.01)
*A61M 16/10* (2006.01)

(52) U.S. Cl.
CPC ........ *A61M 16/021* (2017.08); *A61M 16/042* (2014.02); *A61M 16/0409* (2014.02); *A61M 16/0434* (2013.01); *A61M 16/0445* (2014.02); *A61M 16/0477* (2014.02); *A61M 16/0486* (2014.02); *A61M 16/0488* (2013.01); *A61M 16/0493* (2014.02); *A61M 16/208* (2013.01); *A61M 16/0093* (2014.02); *A61M 16/1055* (2013.01); *A61M 16/1065* (2014.02)

(58) Field of Classification Search
CPC .......... A61M 16/0434; A61M 16/0463; A61M 16/0486; A61M 16/0488; A61M 16/0493; A61M 16/208

See application file for complete search history.

(56) References Cited

U.S. PATENT DOCUMENTS

| | | | |
|---|---|---|---|
| 4,166,467 A | | 9/1979 | Abramson |
| 4,300,550 A | | 11/1981 | Gandi et al. |
| 4,595,005 A | | 6/1986 | Jinotti |
| 4,995,388 A | * | 2/1991 | Brain .................... A61M 16/04 128/207.15 |
| 5,339,808 A | | 8/1994 | Don Michael |
| 5,957,134 A | | 9/1999 | Lee |
| 6,631,720 B1 | * | 10/2003 | Brain ................ A61M 16/0486 128/207.14 |
| 2006/0032505 A1 | | 2/2006 | Alfery et al. |

OTHER PUBLICATIONS

Final Office Action, U.S. Appl. No. 12/158,669, dated Jan. 22, 2013, pp. 9.
Non-Final Office Action, U.S. Appl. No. 12/158,669, dated Jul. 25, 2013, pp. 8.

* cited by examiner

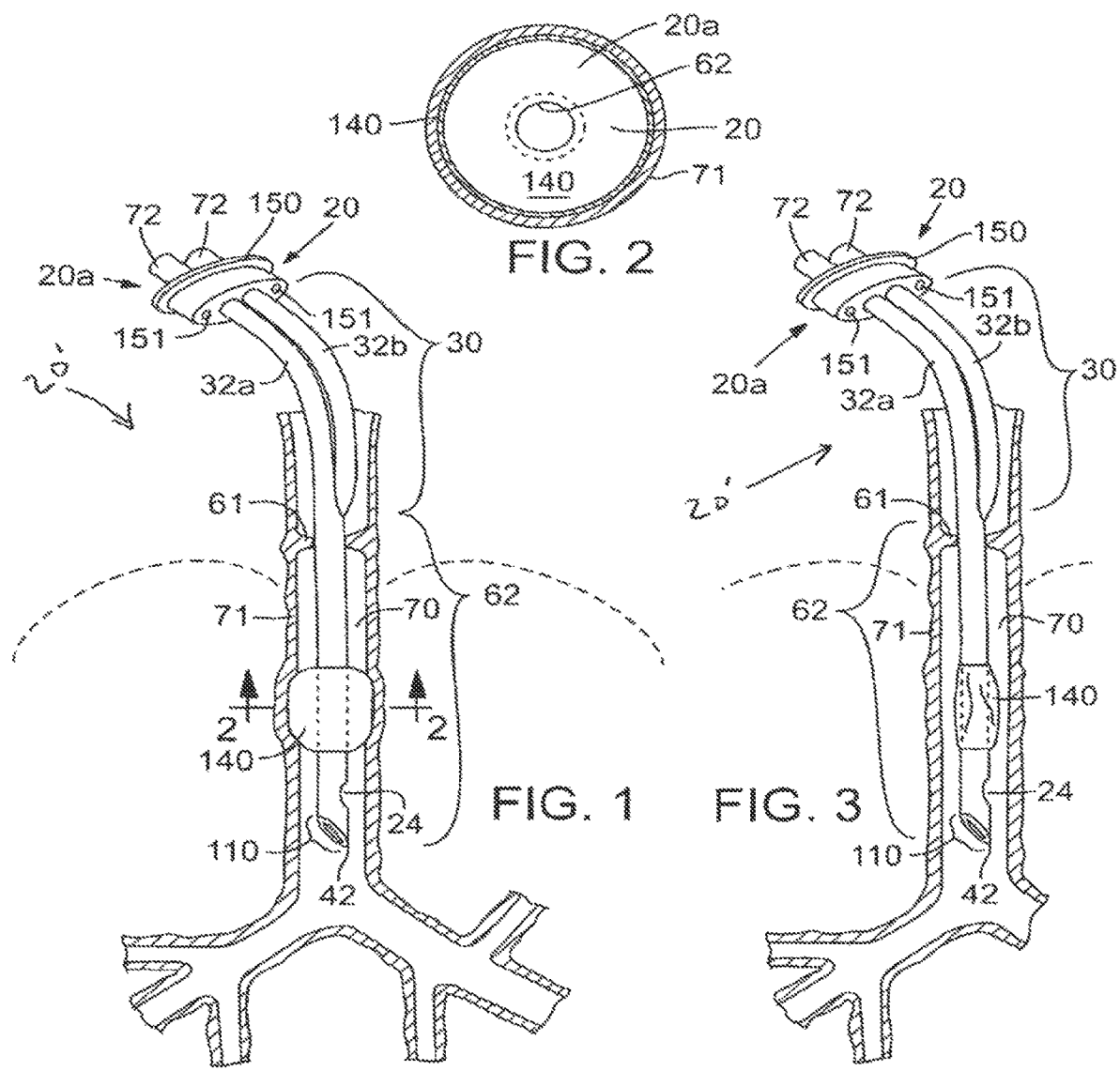

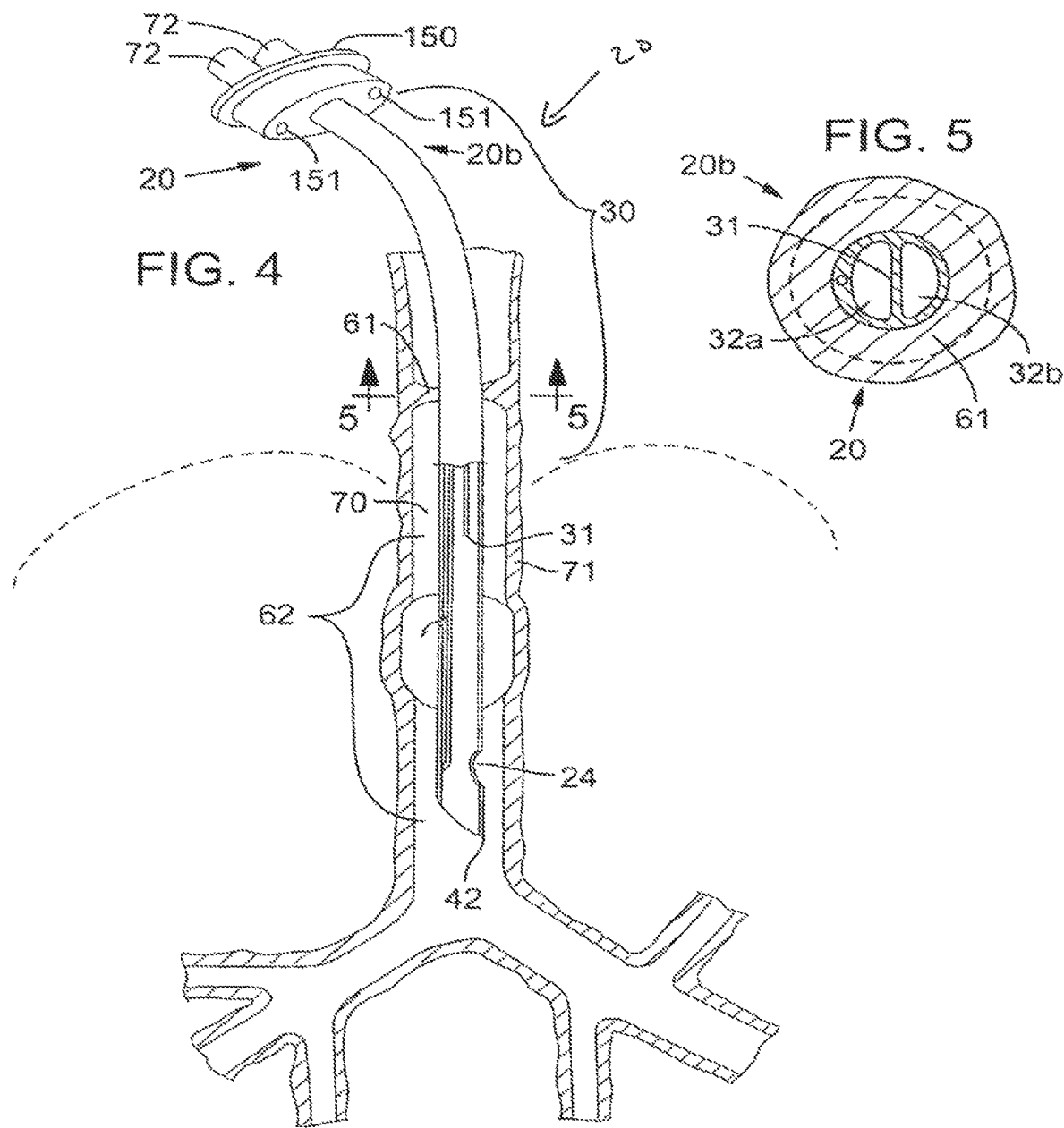

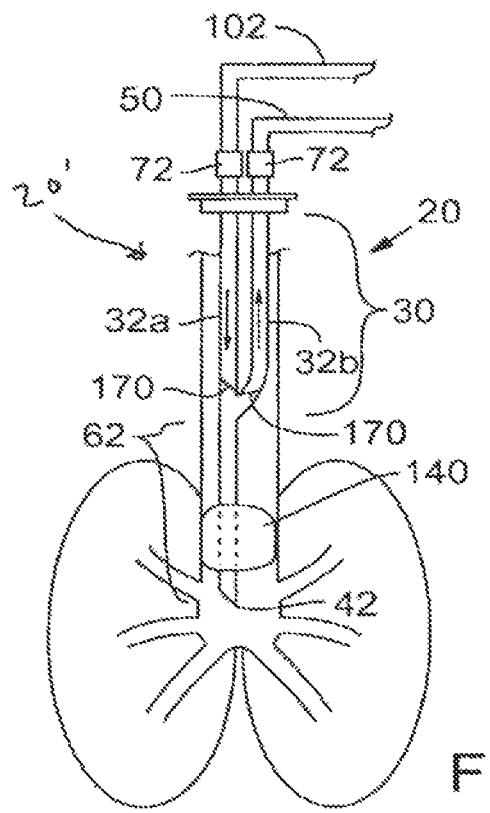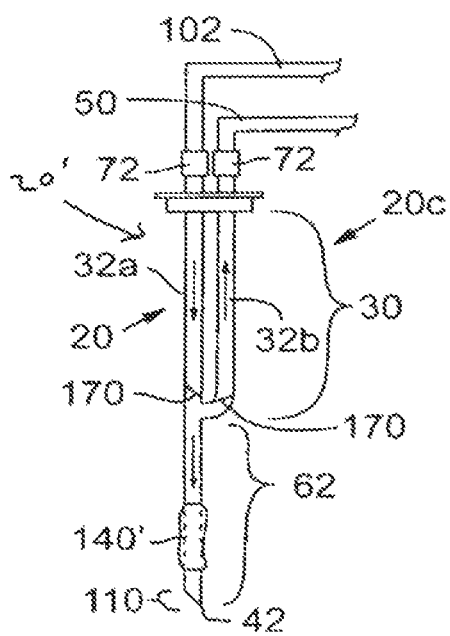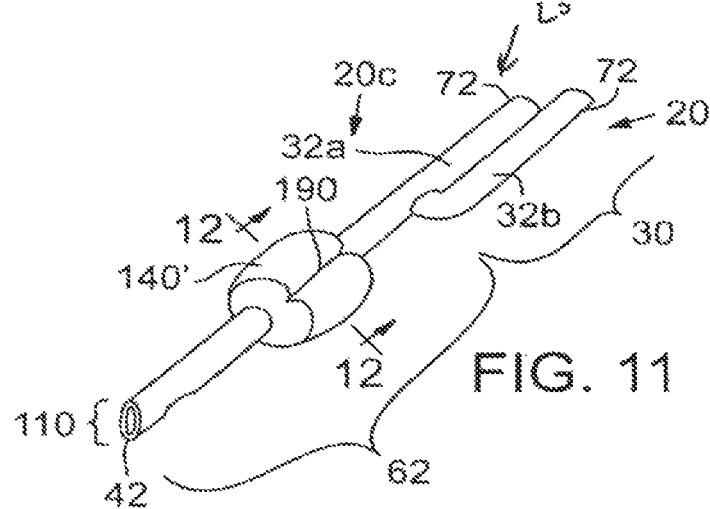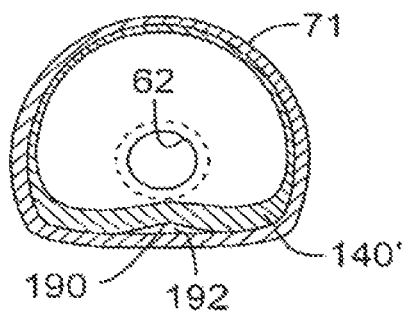
FIG. 9
FIG. 10
FIG. 11
FIG. 12

SECRETION CLEARING PATIENT AIRWAY MANAGEMENT SYSTEM

PRIORITY CLAIM

This application is a continuation of U.S. utility patent application Ser. No. 14/165,317, filed on Jan. 27, 2014, which is a continuation of U.S. utility patent application Ser. No. 12/158,669, filed on Jan. 20, 2009, which is a 371 National Stage Entry of PCT/IB2006/004079, filed Dec. 21, 2006, which claims priority to U.S. Provisional Patent Application Ser. No. 60/752,108, filed on Dec. 21, 2005. The disclosures of U.S. Ser. Nos. 14/165,317, 12/158,669, PCT/IB2006/004079, 60/752,108 and 60/629,074 are hereby incorporated by reference in their entireties as if fully set forth herein.

BACKGROUND OF THE INVENTION

This invention relates to patient airway management systems such as ventilation catheters, which are commonly known as endotracheal tubes, and supraglottic airway systems such as laryngeal masks and the like.

The traditional field of airway management includes a process of controlled ventilation that usually uses a mechanical ventilating machine to deliver a predetermined amount of inspiratory fluid, which is usually an air/oxygen gas mixture, with or without added water vapor, to the lungs of a patient on a predetermined cycle. Usually, the ventilating machine cycles between delivering relatively high-pressure inspiratory fluid via a delivery system to the patient's lungs for a short time, and then reducing the pressure in the delivery system for a short time so that used inspiratory fluid within the patient's lungs is expelled. The ventilating machine repeats this cycle of delivering new inspiratory fluid to and then expelling used inspiratory fluid from a patient's lungs, thereby ensuring proper oxygenation of a patient during times when they are unable to breathe on their own.

More recently, airway management systems have evolved to permit oxygenation of a patient using oxygenated liquids and/or using a non-cyclic process involving a continuous flow of oxygenated liquids to a patient's lungs while simultaneously maintaining a continuous flow of used fluids from the patient's lungs. An example of these types of systems can be found in U.S. Pat. No. 5,706,830 to Parker.

Patient airway management structures such as ventilation catheters and supraglottal-positioned airway structures are commonly used by both traditional and these more recent airway management systems to deliver inspiratory fluid to the patient's lungs. Inspiratory fluid is usually delivered to these structures through a single tube, the internal cavity of which is often referred to as a lumen, that has an open distal end. The distal end is inserted through a patient's mouth and in cases where the structure is a catheter, inserted into the patient's trachea so that the distal end is positioned well past the patient's vocal chords. The opposite end of the endotracheal tube is operably connected to a ventilation machine. Accordingly, inspiratory fluid is provided directly to the lungs through the endotracheal tube and used fluid is removed from the patient's lungs through the same tube.

The endotracheal tube must have a reasonably small cross-section to permit easy insertion and positioning of the tube within a patient's trachea. However, the cross-section must be large enough to allow a sufficient flow of oxygenated fluid therethrough.

To date, efforts to improve the use and operation of endotracheal tubes have focused on solving two problems. First, efforts have focused on improving the security and pneumatic sealing of the endotracheal tube within the trachea. Second, efforts have focused on improving the ability of the endotracheal tube to pneumatically isolate individual lungs and/or bronchial chambers within a lung.

Regarding the first problem, one solution that addresses this issue has been to place an inflatable cuff around the endotracheal tube toward the distal end of the tube. The cuff is deflated during insertion of the tube, and inflated when the tube is properly positioned within the trachea, thereby holding the tube in place and creating a pneumatic seal. An example of these types of cuff structures can be found in FIGS. 1A and 1B of U.S. Pat. No. 6,443,156 to Niklason et al.

While the seal offered by these cuffs reduces the likelihood of a patient's airway being inadvertently contaminated with gastric and pharyngeal fluids, they also seal within a patient's lungs pulmonary secretions and fluids. A typical patient can produces about 200 cubic centimeters to 400 cubic centimeters of pulmonary secretions and fluids a day. The volume of these fluids and secretions tends to increase dramatically if a patient also has a pulmonary infection and/or certain types of cardiac disease.

The usual methods for addressing pulmonary secretion and fluid build-up arising during mechanical ventilation of a patient involve periodic suctioning of the patient's lungs and/or an increased antibiotic treatment to address ancillary infections that arise. Such periodic suctioning increases the risk of damaging a patient's pulmonary system and increases the risk of contaminating a patient's airway during each procedure.

Regarding the second problem, some inventors have attempted to isolate lungs and/or bronchial chambers by providing a plurality of individual lumens within the endotracheal tube. Each tube can have its own pneumatic cuff to allow isolation of particular lungs and/or bronchial tubes. However, each tube operates much like a single lumen tube, by providing both inspiratory fluid to the lung and removing used inspiratory fluid from the lung. These types of structures still allow pulmonary secretions and fluids to build-up in the lungs, and the traditional secretion removal and treatment methods must still be employed. Moreover, the cross section of the endotracheal tube can be rather large, thereby limiting the usefulness of the tube in small airways, such as on children and infants.

More recently, supraglottic-positioned airway structures have been developed. One such structure is commonly referred to as a laryngeal mask. It usually has an inflatable mask and resilient tube that connects to the inspiratory fluid delivery system. The mask is inserted in the patient's pharynx, forming a low pressure seal around the laryngeal inlet thereby permitting positive pressure ventilation. Exemplar laryngeal mask structures can be found in U.S. Pat. No. 7,140,368 to Collins and U.S. Pat. No. 5,632,271 to Brain, the disclosures of which are hereby incorporated by reference.

A similar structure can be found in U.S. Pat. No. 5,819,733 to Bertram, which is hereby incorporated by reference. It discloses a transpharyngeal-positioned inspiratory fluid delivery tube with pharyngeal and esophageal inflatable cuffs positioned therealong. Once the tube is inserted into the patient's esophagus, the esophageal cuff is inflated to isolate the patient's gastric system. Then the pharyngeal cuff is inflated within the patient's pharynx, thereby isolating the patient's airway to the inspiratory fluid delivery tube.

Despite the benefits of these supraglottic-mounted airway structures, they still have similar drawbacks to those found in conventional endotracheal tubes. For example, they do not effectively remove pulmonary fluids and debris from the patient's airway.

SUMMARY OF THE INVENTION

Accordingly, despite the benefits offered by known patient airway management systems such as ventilation catheters, laryngeal masks, and the like, there is still a need for a compact airway management system that can be easily inserted within a patient that allows for the easy removal of pulmonary secretions and liquids without the need for periodic auxiliary suctioning and the like. In addition to other benefits described herein, the present invention fulfills these needs.

In one disclosed embodiment, the pulmonary secretion clearing airway management systems is a ventilation catheter has a double lumen portion with each lumen of the double lumen portion operably secured to an airway management system so that inspiratory fluid (air/oxygen mixtures, with or without added water vapor) is delivered to the distal end of the ventilation catheter through one of the two lumens and expired inspiratory fluid, pulmonary secretions, and pulmonary fluids are removed from the patient through the other lumen.

The used inspiratory fluid pathway preferably includes a secretion collection system for removing the pulmonary secretions and the like from the pathway thereby improving operation and safety of the system. In addition, by containing the used inspiratory fluid within the system, rather than releasing it to the environment, the release of potentially airborne infective material from a contagious patient, such as SARS and the like, can be minimized.

An improved cuff can also be used. The cuff encircles the distal end of the ventilation catheter to form a substantially pneumatic seal within the trachea. A small channel is formed along one side of the vent so as to allow a small leakage of air from the lungs of the patient during use to the ventilation catheter. This air leakage facilitates removal of secretions from within the patient's lungs without interfering with the ventilation catheter.

Alternative embodiments include incorporating the double lumen structure into a supraglottic-positioned airway structure such as a laryngeal mask or a transpharyngeal-positioned inspiratory fluid delivery tube with pharyngeal and esophageal inflatable cuffs positioned therealong.

A regurgitation alerting system is also provided.

Other advantages and features of the present invention will become clear upon study of the following portion of this specification and drawings.

BRIEF DESCRIPTION OF THE DRAWINGS

FIG. 1 is an isometric view of a first preferred ventilation catheter having a first inflatable cuff in an inflated configuration in accordance with an embodiment of the present invention and showing a possible installation within a cut-away view of a patient's trachea.

FIG. 2 is a cross sectional view of the ventilation catheter of FIG. 1 taken along line 2-2 of FIG. 1.

FIG. 3 is the ventilation catheter of FIG. 1 showing the first inflatable cuff deflated.

FIG. 4 is an isometric view of a second preferred ventilation catheter having a first inflatable cuff in an inflated configuration in accordance with an embodiment of the present invention.

FIG. 5 is a cross-sectional view of the ventilation catheter of FIG. 4 taken along line 5-5 of FIG. 4.

FIG. 9 is a schematic diagram of a third preferred ventilation catheter in accordance with an embodiment of the present invention.

FIG. 10 is the third preferred ventilation catheter of FIG. 8 showing a cuff in a possible deflated position.

FIG. 11 is an isometric view of a fourth preferred ventilation catheter showing a second preferred cuff operably attached thereto.

FIG. 12 is a cross-section view of the fourth preferred ventilation catheter of FIG. 11 taken along line 12-12 of FIG. 11.

DETAILED DESCRIPTION

Figure 6:
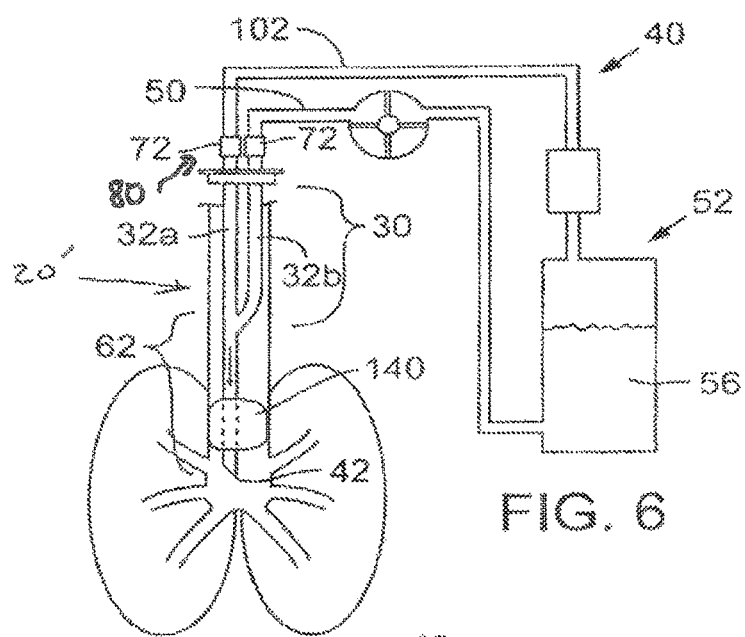
FIG. 6 is a schematic diagram of an airway management system with a ventilation catheter of FIG. 1 in accordance with an embodiment of the present invention.

A pulmonary patient airway delivery structure 20 for use with an airway management system 40 is disclosed in FIGS. 1-19. FIGS. 1-19 show the airway delivery structure 20' in the form of a ventilation catheter. FIGS. 14-18 show the airway delivery structure 20" in the form of a laryngeal mask, and FIG. 19 show the airway delivery structure 20''' in the form of transpharyngeal-positioned inspiratory fluid delivery tube with pharyngeal and esophageal inflatable cuffs positioned therealong. Each of these embodiments is discussed in greater detail below. In order to reduce undue repetition like elements between these embodiments are like numbered.

Referring to FIGS. 1-13, the secretion clearing ventilation catheter 20' and related airway management system 40 are disclosed. In general, the ventilation catheter 20', which is also referred to as an endotracheal tube, extends into the trachea 24 of a patient to provide ventilation. The ventilation catheter 20' has a double lumen portion 30. Each lumen 32a, 32b of the double lumen portion 30 is operably secured to an airway management system 40 (FIGS. 6-8) so that inspiratory fluid (air/oxygen mixtures, with or without added water vapor) is delivered to the distal end 42 of the ventilation catheter 20 through one of the two lumens 32a, 32b (here 32a is shown) and expired inspiratory fluid, pulmonary secretions, and pulmonary fluids are removed from the patient through the other lumen 32a, 32b (here 32b is shown).

Separating the incoming and outgoing inspiratory fluid flow through separate lumens 32a, 32b prevents the fresh incoming inspiratory fluid from becoming blocked or contaminated by inadvertent pulmonary secretions and fluids mixed with the used inspiratory fluid. The used inspiratory fluid pathway 50 (FIGS. 6-8) preferably includes a secretion collection system 52 for removing the pulmonary secretions and the like from the pathway 50, thereby improving operation and safety of the system. In addition, by containing the used inspiratory fluid within the system, rather than releasing it to the environment, the release of potentially airborne infective material from a contagious patient, such as SARS and the like, can be minimized.

Several ventilation catheter embodiments having these basic features are disclosed in this application. In order to reduce undue repetition like elements between these embodiments have like element numbers.

Preferably and referring to FIG. 1, a first preferred ventilation catheter 20a is disclosed. In this embodiment, the double lumen portion 30 is positioned at the pre-pharyngeal/pharynx region of the patient upstream of their vocal chords 61. Each lumen 32a, 32b of the double lumen portion 30 pneumatically joins together to form a single lumen portion 62 that extends toward the distal end 42 of the ventilation catheter 20a. The single lumen portion 62 protrudes into the intratracheal region 70 of the patient. This allows a small diameter single lumen portion 62 to extend past the vocal chords into the trachea of the patient, while still allowing the secretion clearing benefits of the double lumen portion 30. The double lumen portion 30 positioned in the pre-pharyngeal level increases the efficiency of ventilation, reduces unnecessary dead space, eliminates secretions, and permits a smaller diameter intratracheal catheter to be used.

Preferably, each lumen 32a, 32b of the double lumen portion 30 has a proximal end 80 to which are connected conventional adapters 72 for detachable securing to mating connectors on a conventional ventilation system 40 (FIG. 6). One lumen 32a is connected through its connector to a delivery conduit 102 of a conventional ventilation system 40 (FIG. 6). The other lumen 32b is connected to the used inspiratory fluid pathway 50 of the ventilation system 40. The system 40 is controllable for delivering inspiratory fluid at pre-selected flow rates. The inspiratory fluid is thus delivered to the proximal end of lumen 32a at a pressure of about 20 mmHg for a selected period of time. After which, the system is vented in a way to drop the pressure in the system to about 6 mmHg during the expiratory phase of the ventilation cycle. This causes fluid, along with pulmonary secretions and pulmonary fluids to exit the patient through the second lumen 32b.

More preferably, the ventilation system 40 is configured to deliver inspiratory fluid through one lumen 32a of the double lumen portion 30 on inspiration while used inspiratory fluid and secretions are expelled from the patient through the other lumen 32b of the double lumen portion 30 during both inspiration and expiration phases of the ventilation system 40.

The tip 110 of the ventilation catheter 20a is preferably beveled and softened usefully to assist in the passage of the single lumen portion during the intubation of the trachea. The tip is preferably designed to resist the backward bending that might obstruct the airway.

The double lumen portion and single lumen portion of the ventilation catheter are preferably made of a soft, clear medically approved elastomer. If desired and referring to FIG. 9, one-way check-valves 170, such as flapper valves, can be posited within one or both lumens of the double lumen portion to further prevent back-flow through these lumens.

Preferably, a low pressure, inflatable cuff 140 is positioned toward the distal end 42 of the ventilation catheter. The inflatable cuff 140 is preferably made of a thin film of substantially impermeable plastic or the like. The edges of the cuff are bonded to the outer surface of the single lumen portion 62. The cuff 140 is inflated with known means, such as those disclosed in FIGS. 1A and 1B of U.S. Pat. No. 6,443,156, which involves extending a cuff inflation line within the ventilation catheter 20a from the cuff 140 to an auxiliary inflator.

The ventilation catheter 20a is inserted into a patient's trachea 24 when the cuff 140 is deflated as shown in FIG. 3. Then, the cuff 140 is inflated. Once inflated, the cuff 140 expands as shown in FIGS. 1 and 2 to assume the substantially circular cross-sectional shape of the trachea, thereby pneumatically sealing the patient's lungs to the ventilation catheter 20a.

Preferably, a durable, bite-resistant, bite block 150 is secured to the double lumen portion of the ventilation catheter as shown in FIG. 1. Each lumen 32a, 32b of the double lumen portion 30 extends though the bite block 150. More preferably, the bite block 150 is slidably secured to the double lumen portion 30 so as to allow the position of the bite block 150 relative to a patient's teeth and lips to be adjusted as needed by sliding the bite block along the double lumen portion. More preferably, the bite block 150 includes one or more auxiliary holes therethrough or the like that are in parallel with the double lumen portion 30. These holes can be used as needed for endo-bronchial blocking catheters, fiberoptic endoscopes, and the like. Vent holes 151 can also be provided as needed.

Figures 7, 8:
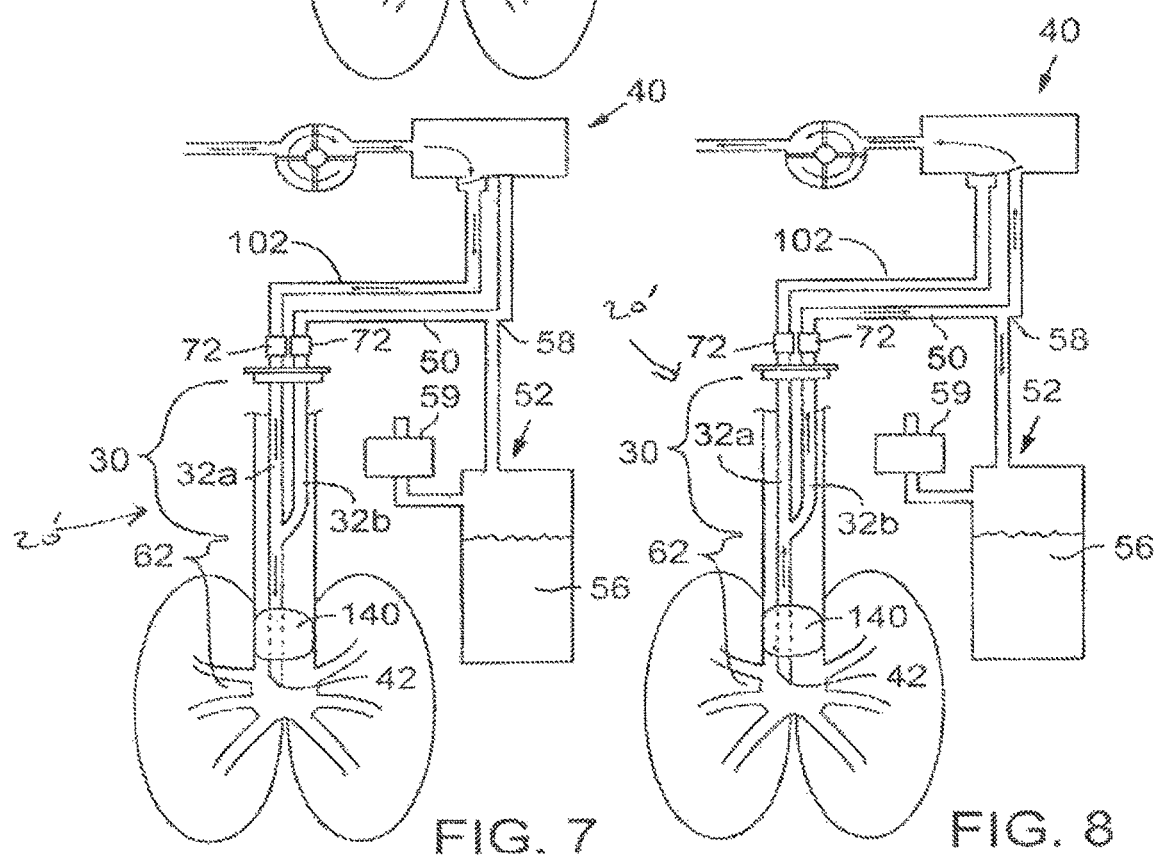
FIG. 7 is a schematic diagram of an alternative preferred airway management system in accordance with an embodiment of the present invention showing a possible flow circuit of oxygenated fluid to a patient's lungs.
FIG. 8 is the schematic diagram of FIG. 7 showing a possible discharge circuit from the patient's lungs through the airway management system.

Preferably, the ventilation system 40 (FIG. 6) is adapted as shown in FIGS. 7 and 8 to include a secretion collection system 52 in the outflow circuit. The secretion collection system 52 preferably includes a secretion collection chamber 56 in pneumatic communication with the used inspiratory fluid pathway 50 at a diverter 58. As secretions in the used inspiratory fluid pathway 50 pass by the diverter 58, they are directed toward the collection chamber 56 either by gravity, or with the assistance of an auxiliary pump 59.

One or more ultraviolet light generating bulbs may be placed in the flow path(s) to provide desired antibacterial activity as needed. Similarly, an appropriate antibacterial/anti-virus filter can be posted within the system to prevent exhaust gasses and the like from being released into the environment.

Referring to FIGS. 4 and 5, a second preferred ventilation catheter 20b is shown. In this embodiment, the double lumen portion 30 is formed by a longitudinal wall 31 extending down the middle of a single lumen to define two lumens 32a, 32b. The wall 31 is removed toward the distal end 42 of the ventilation catheter 20b thereby combing the two lumens 32a, 32b into a single lumen portion 62. As with the first preferred ventilation catheter 20a (FIGS. 1-3), oxygenate fluid in this embodiment 20b, is delivered through one lumen 32a to the single lumen portion 62, and used inspiratory fluid is removed from the patient through the second lumen 32b.

Referring to FIGS. 10 and 11, a third preferred ventilation catheter 20c is shown. In this embodiment, the double lumen portion 30 is formed by a single lumen extending down the entire length of the ventilation catheter 20c, thereby defining a substantially straight channel through which to insert auxiliary devices, such as fiberoptic endoscopes, and the like. The second lumen 32b of the double lumen portion 30 intersects the single lumen substantially at a right angle as shown thereby defining the double lumen portion 30 of the ventilation catheter 20c.

As best shown in FIGS. 11 and 12, an alternative preferred lower pressure, inflatable cuff 140' is positioned toward the distal end 42 of the ventilation catheter 20c. The alternative preferred inflatable cuff 140' is preferably made of a thin film of substantially impermeable plastic or the like. The edges of the cuff are bonded to the outer surface of the single lumen portion 62, and a recessed channel 190 is provided on one side of the inflated cuff 140'.

The cuff 140' is inflated with known means, such as those disclosed in FIGS. 1A and 1B of U.S. Pat. No. 6,443,156, which involves extending a cuff inflation line within the ventilation catheter from the cuff to an auxiliary inflator.

The ventilation catheter 20c is inserted into a patient's trachea 24 without the cuff 140' inflated. Then, the cuff 140' is inflated. Once inflated, the cuff expands as shown in FIGS. 11 and 12 to assume the substantially circular cross-sectional shape of the trachea 24, thereby substantially pneumatically sealing the patient's lungs to the ventilation catheter. The recessed channel 190 allows a small pneumatic opening 192 between the cuff 140' and the trachea wall 71, thereby allowing a limited pneumatic leak from the patient's lungs to the environment. Preferably, the channel 190 is sized so as to allow about 10% of the inspiratory fluid delivered through the ventilation catheter 20c to exit through the pneumatic opening 192.

This continuous leaking facilitates secretion clearing of the lungs. Pulmonary secretions and the like travel up the trachea through the pneumatic opening 192 in the cuff 141' to the patient's hypopharynx, where they can be easily suctioned way without disruption the ventilation catheter.

Figure 13:
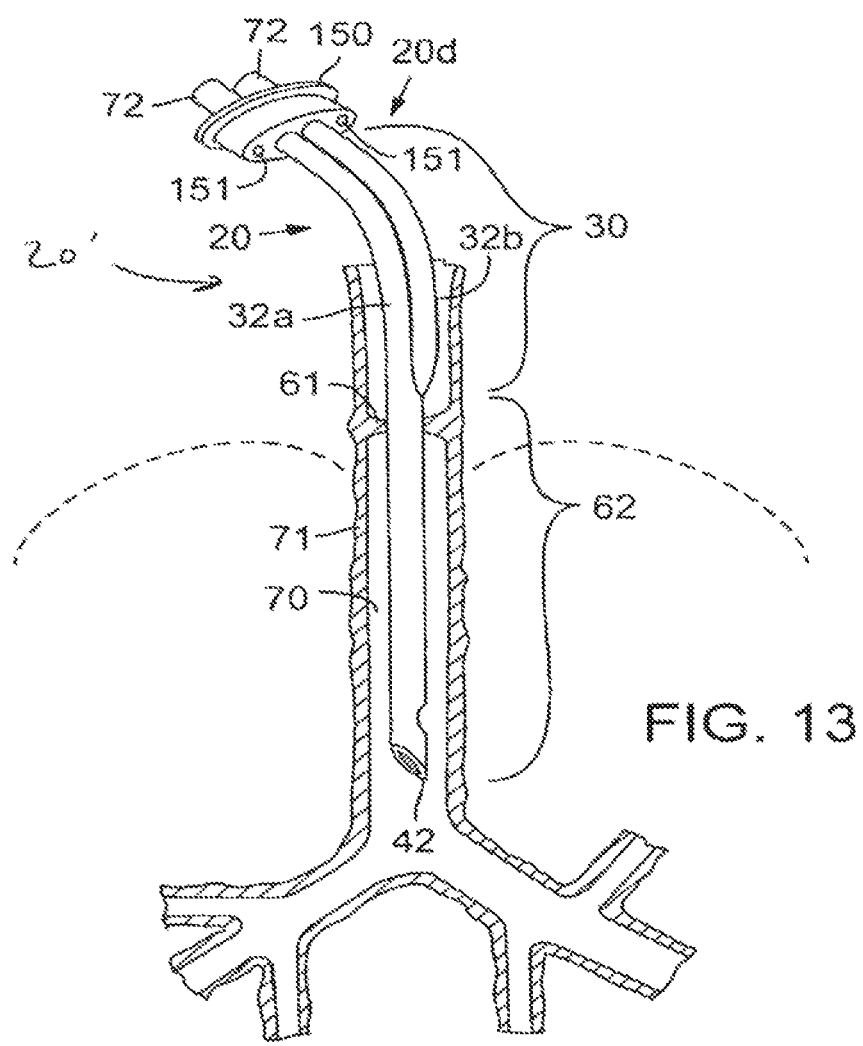
FIG. 13 is an isometric view of a fifth preferred ventilation catheter in accordance with an embodiment of the present invention.

Referring to FIG. 13, a fourth ventilation catheter 20 d is disclosed. This catheter is substantially similar to the first disclosed embodiment of FIG. 1, but does not have an inflatable cuff 140 (FIG. 1) operably secured thereto. This cuffless design is particularly useful when working in small tracheas, such as those found in infants and small children.

Referring to FIGS. 14-18, the airway delivery structure 20 of the present invention is shown in the form of a laryngeal mask 20" which preferably has a traditional inflatable bowl 200 or the like that is operably secured to a preferably flexible tube portion 202. The tube portion 202 preferably has a double lumen portion 30. Each lumen 32a, 32b of the double lumen portion 30 is operably secured to an airway management system 40 (FIGS. 17-18) so that inspiratory fluid (air/oxygen mixtures, with or without added water vapor) is delivered to the distal end 42 of the bowl 200 through one of the two lumens 32a, 32b (here 32a is shown) and expired inspiratory fluid, pulmonary secretions, and pulmonary fluids are removed from the patient through the other lumen 32a, 32b (here 32b is shown).

Figure 17:
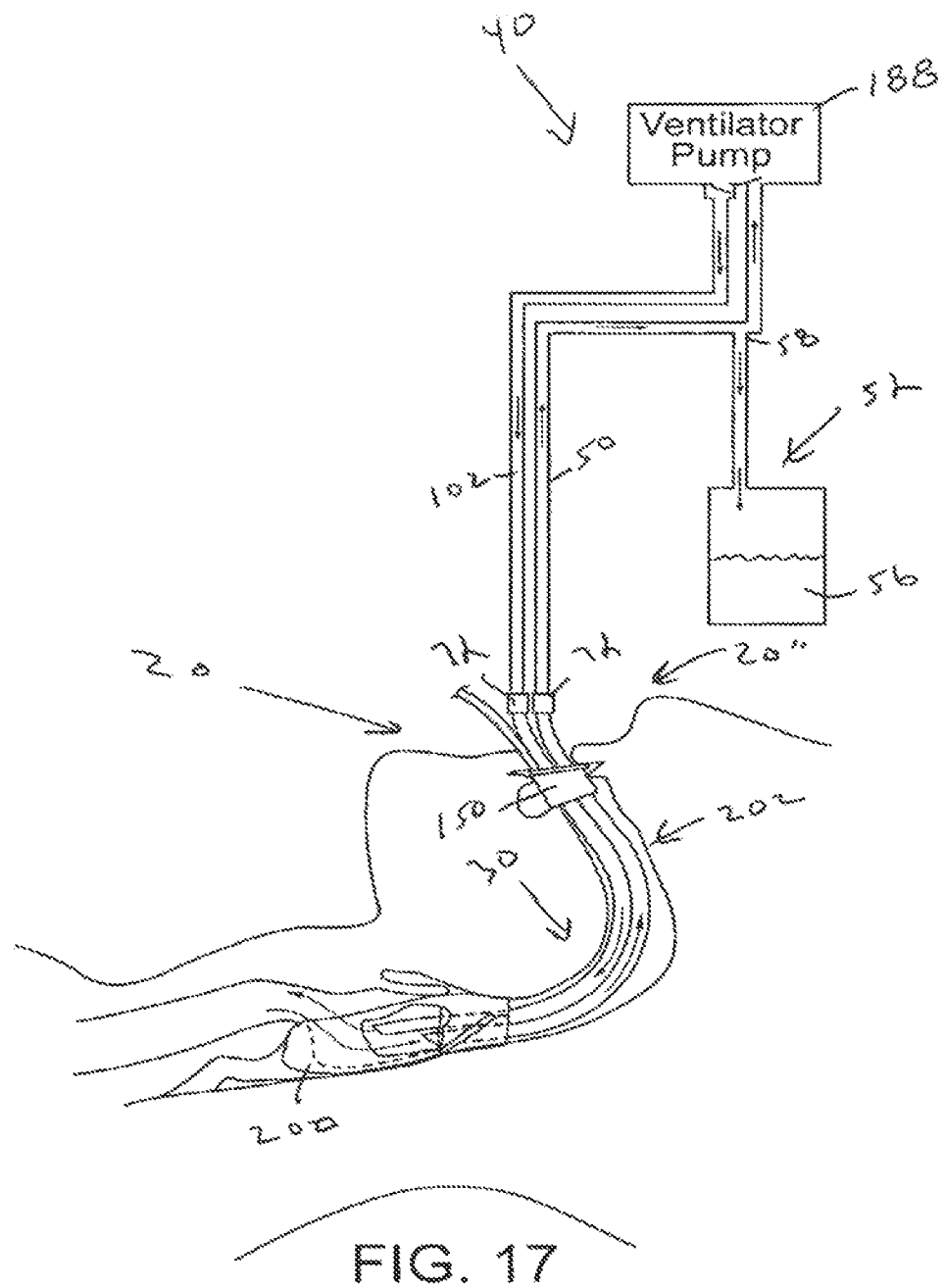
FIG. 17 is a schematic diagram of an airway management system with the laryngeal mask of FIG. 14 in accordance with an embodiment of the present invention.

Preferably, the distal end of lumen 32a extends into the bowl and is spaced forward from and above the distal end of lumen 32b during use in a patient as best shown in FIG. 17. Accordingly, pulmonary fluids and the like that pool in the bowl 200 and are easily removed through lumen 32b without interfering with incoming inspiratory fluid delivery through lumen 32a. More preferably, each distal end of the lumens 32a, 32b are tapered as shown in FIG. 17.

Figure 14:
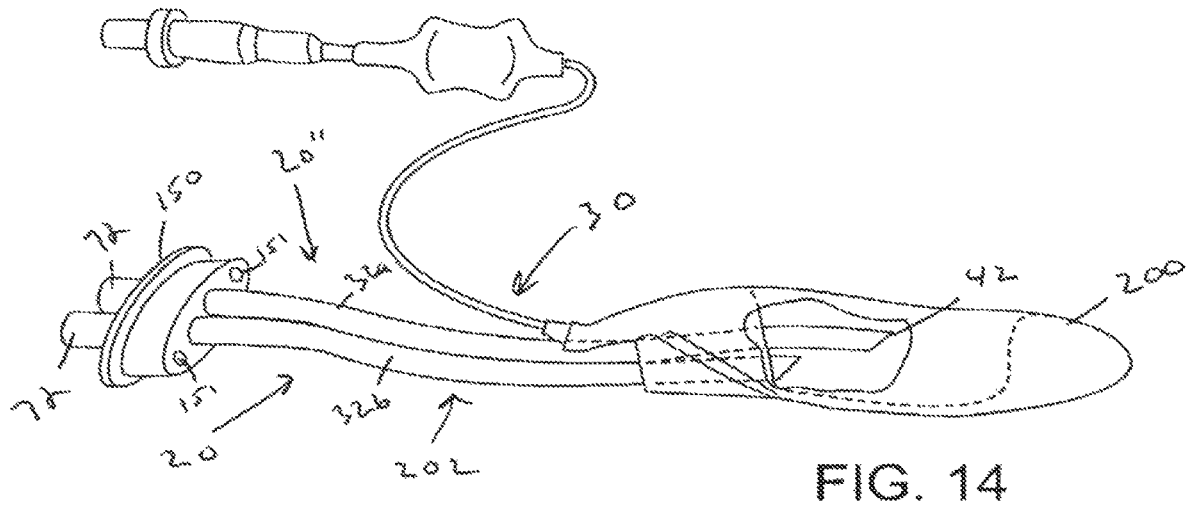
FIG. 14 is an isometric view of a laryngeal mask in accordance with an embodiment of the present invention with a portion of the bowl cut-away to show possible internal detail.
Figure 15:
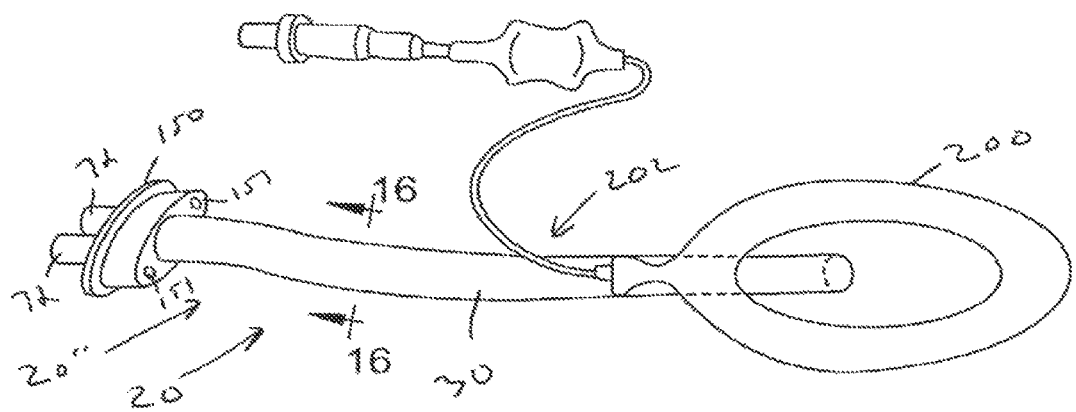
FIG. 15 is an isometric view of an alternative preferred laryngeal mask in accordance with an embodiment of the present invention.
Figure 16:
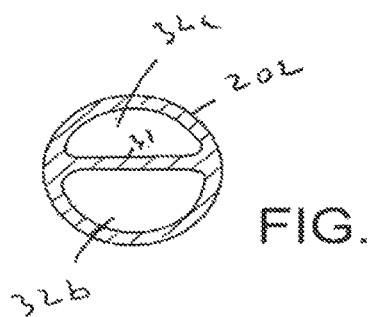
FIG. 16 is a cross sectional view of the alternative preferred laryngeal mask of FIG. 15 taken along line 16-16 of FIG. 15.
Figure 18:
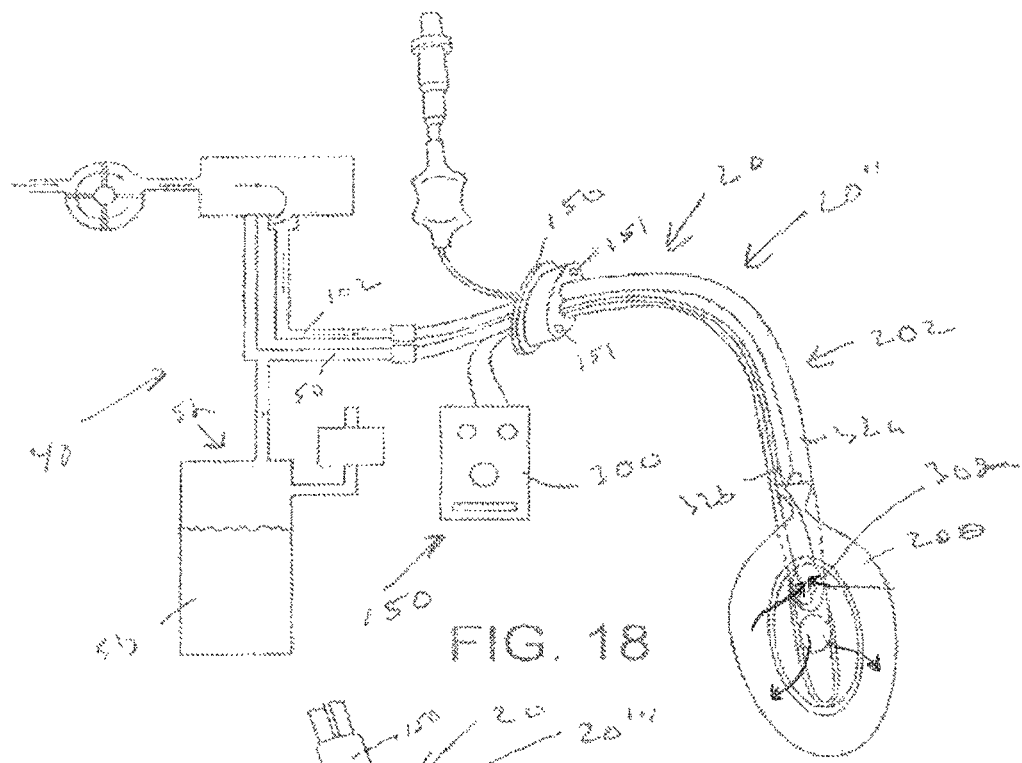
FIG. 18 is a schematic diagram of an alternative airway management system with the laryngeal mask of FIG. 14 showing a possible regurgitation alert system operably secured thereto.
Figure 19:
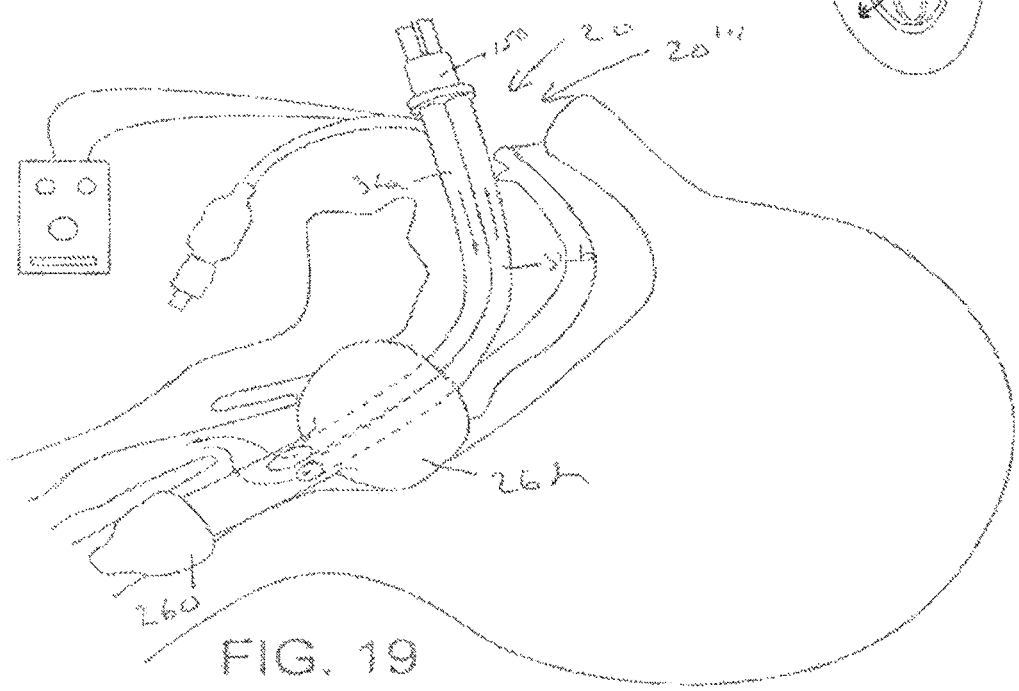
FIG. 19 is an schematic diagram of an airway management system with a transpharyngeal-positioned inspiratory fluid delivery tube with pharyngeal and esophageal inflatable cuffs positioned therealong in accordance with an embodiment of the present invention.

The lumens 32a, 32b of the double lumen portion 30 can be formed by securing two tubes together as shown in FIGS. 14, 17 & 18, or the double lumen portion 30 is formed by a longitudinal wall 31 extending down the middle of a single lumen to define two lumens 32a, 32b as shown in FIGS. 15 & 16.

Preferably, a regurgitation alerting system 150 is also provided. Referring to FIG. 18, a possible regurgitation alerting system is shown having a computer system 180 in electrical communication with an acid sensor 302 positioned toward the distal end of the laryngeal mask. The computer system 300 is preferably a conventional structure having a power source, processor, at least one transducer, memory and the like to receive signals from the sensor, process it, and alert a worker when stomach acid or the like is present in the bowl. The computer system 300 is preferably in communication with the ventilator pump 188 (FIG. 18). Accordingly, it can initiate a bowl cleaning operation, such as by extending the inflow while simultaneously activating the outflow thereby preventing the detected stomach acid from entering the patient's airway. Possible sensors include acid detectors and a light mediated foreign material detection sensor.

Referring to FIG. 19, the airway delivery structure 20 of the present invention is shown in the form of a transpharyngeal-positioned inspiratory fluid delivery tube 20''' with pharyngeal and esophageal inflatable cuffs 260, 262, respectively, positioned therealong. The tube 20''' preferably has a double lumen portion 30. Each lumen 32a, 32b of the double lumen portion 30 is operably secured to an airway management system 40 (See FIGS. 6-8, 17 and 18) so that inspiratory fluid (air/oxygen mixtures, with or without added water vapor) is delivered to the end 42 lumen 32a, between the pharyngeal and esophageal inflatable cuffs 260, 262, respectively, into the patient's airway. Expired inspiratory fluid, pulmonary secretions, and pulmonary fluids are removed from the patient through the other lumen 32b.

The lumens 32a, 32b of the double lumen portion 30 can be formed by securing two tubes together as shown in FIG. 18, or the double lumen portion 30 is formed by a longitudinal wall extending down the middle of a single lumen to define two lumens 32a, 32b.

Separating the incoming and outgoing inspiratory fluid flow through separate lumens 32a, 32b prevents the fresh incoming inspiratory fluid from becoming blocked or contaminated by inadvertent pulmonary secretions and fluids mixed with the used inspiratory fluid. The used inspiratory fluid pathway 50 (FIGS. 6-8, 17 & 18) preferably includes a secretion collection system 52 for removing the pulmonary secretions and the like from the pathway 50, thereby improving operation and safety of the system. In addition, by containing the used inspiratory fluid within the system, rather than releasing it to the environment, the release of potentially airborne infective material from a contagious patient, such as SARS and the like, can be minimized.

While the present invention has been described in terms of preferred embodiments, it will be appreciated by one of ordinary skill that the spirit and scope of the invention is not limited to those embodiments. For example, the alternative preferred cuff 140' (FIGS. 10 & 11) and/or check valves 170

(FIG. 9) could be installed on any disclosed embodiment. Also, an outflow channel may be provided on any of the disclosed structures to permit removal of gastric acid reflux material from the hypopharynx. Accordingly, the scope of the present invention extends to the various modifications and equivalents as defined in the appended claims.

The invention claimed is:

1. A laryngeal mask for operably securing a patient to an airway management system that has a new inspiratory fluid path and an expiratory fluid path, said laryngeal mask comprising:
    an opening toward a distal end of the laryngeal mask for allowing new inspiratory fluid from the airway management system to flow into a patient and used inspiratory fluid from the patient to flow back to the airway management system;
    an inflatable bowl toward the distal end of the laryngeal mask;
    a double lumen portion defining a first lumen configured to be pneumatically connected to the airway management system to provide an inspiratory fluid pathway for the new inspiratory fluid and a second lumen, configured to be pneumatically connected to the airway management system to provide an expiratory fluid pathway for the used inspiratory fluid, the first lumen configured to occupy the prepharyngeal/pharynx region; and
    the first lumen and the second lumen comprising two separate tubes and said double lumen portion sized to be positioned upstream of the patient's vocal chords, and wherein a distal end of said first lumen extends farther into the bowl towards the distal end of the laryngeal mask than a distal end of said second lumen, and the second lumen is positioned closer to the bottom of the bowl than the first lumen.

2. The laryngeal mask of claim 1, further including a bite protector slidably secured to the double lumen portion.

3. The laryngeal mask of claim 1, wherein said expiratory fluid pathway further includes a secretion collector for collecting pulmonary secretions and pulmonary fluids collected from the patient through the expiratory fluid pathway.

4. The laryngeal mask of claim 3, wherein said secretion collector includes a secretion chamber for collecting secretions therein.

5. The laryngeal mask of claim 1, further including a check valve operably secured to at least one of said first lumen and said second lumen to prevent inadvertent pneumatic back flow.

6. The laryngeal mask of claim 5, further including a second check valve operably secured to the other of said at least one of said first lumen and said second lumen.

7. The laryngeal mask of claim 1, further including a check valve in the second lumen thereby preventing inadvertent backflow from the expiratory fluid path toward the distal end of the laryngeal mask.

8. The laryngeal mask of claim 1, further including a regurgitation monitor operably secured thereto.

9. The laryngeal mask of claim 8, wherein said regurgitation monitor includes a sensor in communication with a computer system.

10. The laryngeal mask of claim 8, wherein said computer system is in communication with a ventilator pump and said computer system is configured to modulate said ventilator pump in response to a detected presence of regurgitation.

* * * * *